US009766195B2

(12) United States Patent
Daamen et al.

(10) Patent No.: US 9,766,195 B2
(45) Date of Patent: Sep. 19, 2017

(54) INTEGRATED CIRCUIT WITH SENSOR AND METHOD OF MANUFACTURING SUCH AN INTEGRATED CIRCUIT

(75) Inventors: Roel Daamen, Herkenbosch (NL); Casper Juffermans, Valkenswaard (NL); Josephus Franciscus Antonius Maria Guelen, Molenhoeck (NL); Robertus Antonius Maria Wolters, Eindhoven (NL)

(73) Assignee: ams International AG, Rappersil-Jona (CH)

( * ) Notice: Subject to any disclaimer, the term of this patent is extended or adjusted under 35 U.S.C. 154(b) by 447 days.

(21) Appl. No.: 13/471,609

(22) Filed: May 15, 2012

(65) Prior Publication Data

US 2012/0299126 A1 Nov. 29, 2012

(30) Foreign Application Priority Data

May 27, 2011 (EP) .................................. 11167866

(51) Int. Cl.
 *H01L 27/20* (2006.01)
 *H01L 41/22* (2013.01)
 (Continued)

(52) U.S. Cl.
 CPC ....... *G01N 27/223* (2013.01); *G01R 31/2881* (2013.01); *G01R 31/2884* (2013.01)

(58) Field of Classification Search
 CPC ................................. H01L 27/20; H01L 41/22
 (Continued)

(56) References Cited

U.S. PATENT DOCUMENTS 4,057,823 A 11/1977 Burkhardt et al.
6,167,834 B1 * 1/2001 Wang et al. .............. 118/723 E
(Continued)

FOREIGN PATENT DOCUMENTS

CN 101034683 A 9/2007
EP 1 950 808 A2 7/2008
(Continued)

OTHER PUBLICATIONS

Extended European Search Report for European patent appln. No. 11167866.0 (Oct. 31, 2011).
(Continued)

*Primary Examiner* — Asok K Sarkar
*Assistant Examiner* — Dmitriy Yemelyanov
(74) *Attorney, Agent, or Firm* — McDermott Will & Emery LLP

(57) ABSTRACT

Disclosed is an integrated circuit (IC) comprising a substrate (10) carrying a plurality of circuit elements; a metallization stack (12, 14, 16) interconnecting said circuit elements, said metallization stack comprising a patterned upper metallization layer comprising at least one sensor electrode portion (20) and a bond pad portion (22), at least the at least one sensor electrode portion of said patterned upper metallization layer being covered by a moisture barrier film (23); a passivation stack (24, 26, 28) covering the metallization stack, said passivation stack comprising a first trench (32) exposing the at least one sensor electrode portion and a second trench (34) exposing the bond pad portion; said first trench being filled with a sensor active material (36). A method of manufacturing such an IC is also disclosed.

10 Claims, 10 Drawing Sheets

Figure 1:
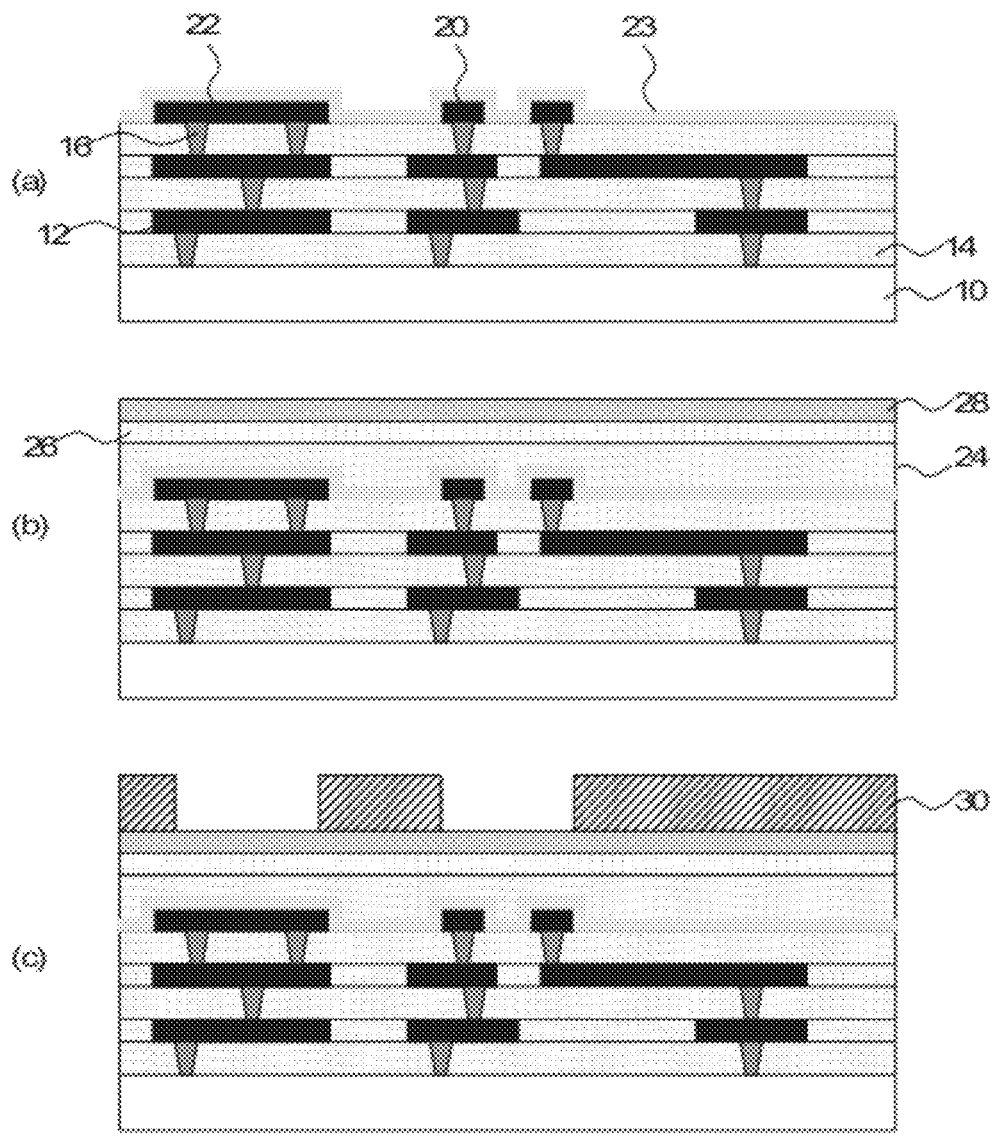
Figure 1:
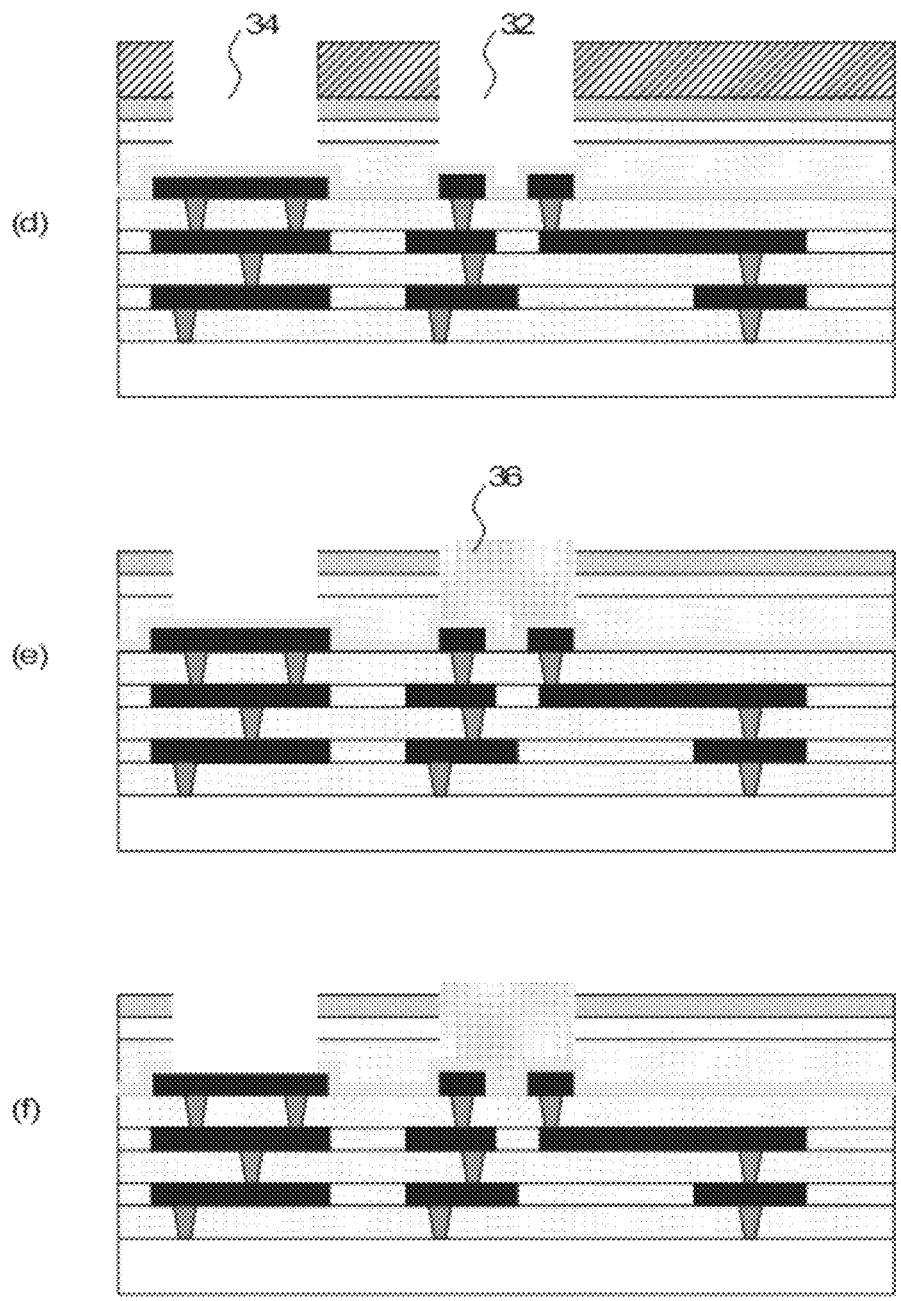

(51) Int. Cl.
*G01N 27/22* (2006.01)
*G01R 31/28* (2006.01)

(58) Field of Classification Search
USPC .............. 257/414, E27.006, E21.598; 438/48
See application file for complete search history.

(56) References Cited

U.S. PATENT DOCUMENTS

| | | | |
|---|---|---|---|
| 6,813,944 | B2 | 11/2004 | Mayer et al. |
| 2006/0064873 | A1* | 3/2006 | Matsuzawa et al. ......... 29/890.1 |
| 2007/0212867 | A1 | 9/2007 | Chen et al. |
| 2011/0012211 | A1* | 1/2011 | Merz et al. ................... 257/415 |
| 2011/0018097 | A1* | 1/2011 | Ponomarev et al. ......... 257/532 |
| 2011/0100810 | A1* | 5/2011 | Merz ............................ 204/406 |
| 2011/0296912 | A1* | 12/2011 | Merz et al. ................. 73/335.05 |

FOREIGN PATENT DOCUMENTS

| | | |
|---|---|---|
| EP | 2 282 333 A1 | 2/2011 |
| EP | 2 284 883 A1 | 2/2011 |
| WO | 2007/036922 A1 | 4/2007 |
| WO | 2010/049881 A1 | 5/2010 |

OTHER PUBLICATIONS

U.S. Appl. No. 13/398,158, filed Feb. 16, 2012.
Office Action from counterpart application 201210162716.2 (Jul. 3, 2014).

\* cited by examiner

US 9,766,195 B2

INTEGRATED CIRCUIT WITH SENSOR AND METHOD OF MANUFACTURING SUCH AN INTEGRATED CIRCUIT

CROSS-REFERENCE TO RELATED APPLICATIONS

This application claims the priority under 35 U.S.C. §119 of European patent application no. 11167866.0, filed on May 27, 2011, the contents of which are incorporated by reference herein.

The present invention relates to an integrated circuit (IC) comprising a substrate carrying a plurality of circuit elements; a metallization stack interconnecting said circuit elements, said metallization stack comprising a patterned upper metallization layer comprising a first metal portion; a passivation stack covering the metallization stack; and a sensor.

The present invention further relates to a method of manufacturing such an IC.

Nowadays, integrated circuits (ICs) may comprise moisture-sensitive sensors, such as relative humidity (RH) sensors or liquid immersion detection sensors. Such sensors may be included in the IC design for a number of reasons.

For instance, such a sensor may be included in the ICs to determine whether a malfunctioning IC that has been returned, e.g. to its manufacturer, has been damaged by exposure to moisture, e.g. an immersion event, or whether the IC itself is faulty. The determination of such external influences as a cause of malfunction may be of crucial importance to deciding whether or not the customer returning the IC or an electronic device including the IC is entitled to a warranty claim on the device, as misuse such as the aforementioned immersion event typically invalidates the warranty.

Alternatively, such a sensor may be part of the functionality of an IC. There is for instance a trend towards providing near-field communication ICs such as radio-frequency (RF) identification (ID) chips with a range of sensors, such as temperature sensors, ambient light sensors, mechanical shock sensors, liquid immersion sensors, humidity sensors, $CO_2$ sensors, $O_2$ sensors, pH sensors and ethylene sensors, which for instance may be used to monitor the ambient conditions of a product tagged with the chip such that product quality control can be achieved by monitoring the sensor readings of the chip.

It is particularly attractive to integrate at least some of these sensors in the back-end of the manufacturing process of an IC, such as in the metallization stack, as this facilitates a cost-effective route to such integration due to the fact that such integration can be achieved with minimal alteration to the process flow.

However, one of the challenges IC designers are faced with when integrating multiple sensors into the metallization stack is that environmental sensors have to be in communicative contact with the environment. This increases the risk that moisture penetrates the metallization stack and interferes with the correct operation of the underlying circuit elements of the IC. To this end, a moisture barrier layer such as a $Ta_2O_5$ layer or a passivation layer may be deposited over the metallization stack to protect the underlying circuitry from exposure to moisture. Unfortunately, when integrating multiple sensors with different functionality in the metallization layer, the partial removal of such a barrier layer cannot always be avoided.

U.S. Pat. No. 4,057,823 discloses an example of an environmental sensor, i.e. a structure for a relative humidity monitor which can be built into an integrated circuit chip. A small area on a silicon chip is made porous by anodic etching. This region is then oxidized and a metal counter electrode is deposited over part of the porous area. Due to the relatively large surface area in the dielectric under the counter electrode and the openness of the structure, ambient moisture can quickly diffuse into the dielectric under the electrode and adsorb onto the silicon dioxide surface, such that changes in ambient humidity will be reflected by measurable changes in capacitance or conductance of the device.

It is clear that there is a desire for the integration of a variety of sensors onto an IC for a number of reasons, some of which have been presented above. However, the integration of moisture-sensitive sensors is not without problems, as it proves difficult to protect the other circuitry of the IC from exposure to moisture, at least in a cost-effective manner.

SUMMARY OF THE INVENTION

The present invention seeks to provide an IC comprising a cost-effective sensor which is protected from moisture penetrating the metallization stack via the sensor.

The present invention further seeks to provide a method of manufacturing such an IC.

According to a first aspect of the present invention, there is provided an integrated circuit (IC) comprising a substrate carrying a plurality of circuit elements; a metallization stack interconnecting said circuit elements, said metallization stack comprising a patterned upper metallization layer comprising at least one sensor electrode portion and a bond pad portion, at least one sensor electrode portion of said patterned upper metallization layer being covered by a moisture barrier film and a passivation stack covering the metallization stack, said passivation stack comprising a first trench exposing the at least one sensor electrode portion and a second trench exposing the bond pad portion; said first trench being filled with a sensor active material.

Such an IC can be manufactured in a cost-effective manner as the standard manufacturing process needs little or no modification for the facilitation of the sensor in the IC design. As the area that is accessible by moisture, i.e. the first trench, is sealed off by a moisture barrier film, e.g. a thin layer of $Ta_2O_5$, either by lining the trench or sealing the entire patterned upper metallization layer apart from the contact surface of the bond pad.

Preferably, the $Ta_2O_5$ film is a chemical vapor deposited film as such films have high conformality and are resistant to cracking, thereby further reducing the risk of moisture penetration into the metallization stack. In addition, the higher dielectric constant of $Ta_2O_5$ (k=22) compared to metallization stack dielectric materials such as $Si_3N_4$ (k=5) further improves the sensitivity of the sensor when covering its electrodes.

In an embodiment, the IC further comprises an etch stop layer directly underneath said patterned upper metallization layer. This has the advantage that in forming the trench the side portions of the at least one electrode portion can also be exposed, thereby improving the sensitivity of the sensor as its contact surface is increased. This is particularly relevant if the at least one sensor electrode portion comprises a pair of electrodes laterally separated by the sensor active material.

In accordance with another aspect of the present invention, there is provided a method of manufacturing an integrated circuit comprising a sensor, comprising providing a substrate carrying a plurality of circuit elements; forming a metallization stack over said substrate interconnecting said circuit elements, said metallization stack comprising a patterned upper metallization layer comprising at least one sensor electrode portion and a bond pad portion; forming a moisture barrier layer covering at least the at least one sensor electrode portion of said patterned upper metallization layer; forming a passivation stack over the metallization stack; patterning the passivation stack to form a first trench exposing the at least one sensor electrode portion and a second trench exposing the bond pad portion; and filling the first trench with a sensor active material.

As will be apparent to the skilled person, the processing steps of the present invention can all be performed using standard processing steps such as CMOS processing steps, such that the manufacturing process of the IC does not require (m)any additional processing steps, thus yielding a cost-effective sensor. Although in a standard IC a moisture barrier film may not be formed, such a film may however be formed using processing technologies, e.g. chemical vapor deposition (CVD), that are already available in a standard process such as a standard CMOS process. A CVD $Ta_2O_5$ film is preferred as the moisture barrier film as such a layer has high conformality and is resistant to cracking even when applied on stepped profiles, as well as for the improved sensitivity of the sensor when covered by the $Ta_2O_5$ film as previously explained.

In an embodiment, the step of forming a metallization stack comprises forming an etch stop layer directly underneath the patterned upper metallization layer, and wherein the step of patterning the passivation stack comprises etching said passivation stack to form the first trench and the second trench, said etching of the first trench terminating on the etch stop layer. This requires a single additional processing step of adding the etch stop layer to the metallization stack formation process, which yields the advantage of being able to expose the side portions of the sensor electrode (s), thus improving sensor sensitivity.

The respective trenches may be sequentially formed. For instance, the method may comprise forming said first trench; forming the moisture barrier layer over the resultant structure; forming a patterned resist layer over the resultant structure, said patterned resist layer exposing a region of the passivation layer over the bond pad portion; forming the second trench; removing the patterned resist layer; and filling the first trench with the sensor active material. This has the advantage of improved control over the trench formation process as the etching of the second trench can otherwise cause overetching of the first trench.

Alternatively, the step of patterning the passivation stack to form a first trench exposing the at least one sensor electrode portion and a second trench exposing the bond pad portion may comprise simultaneously opening the first trench and the second trench. This embodiment is particularly attractive if an overetch of the first trench is acceptable, as it simplifies the manufacturing process, thereby further reducing the cost of the IC with the sensor.

BRIEF DESCRIPTION OF THE EMBODIMENTS

Figure 2:
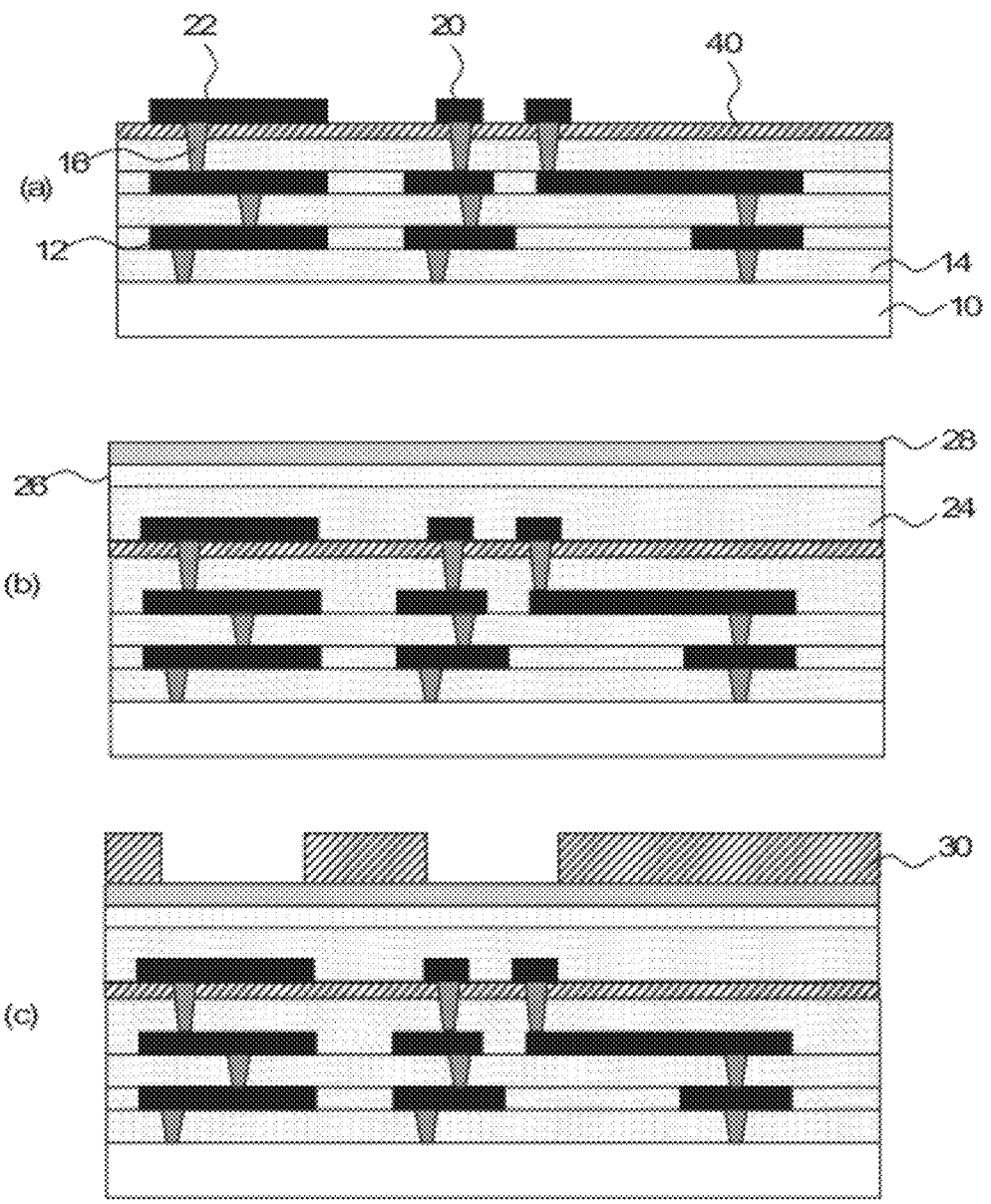
Figure 2:
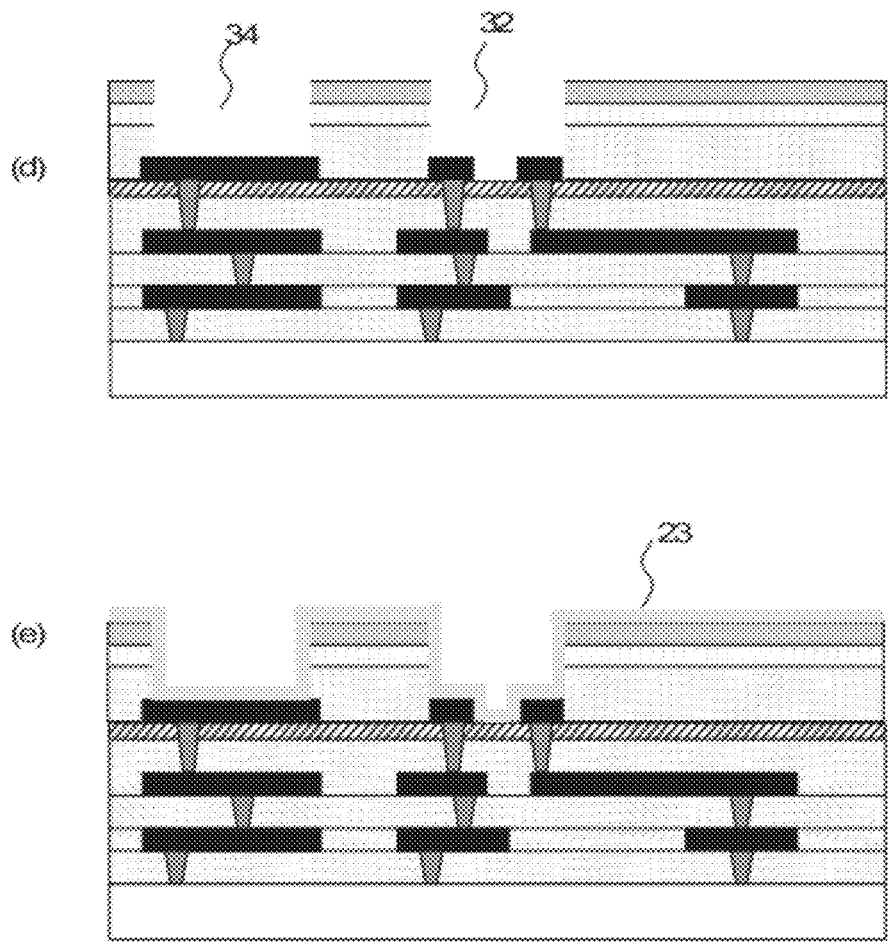
Figure 2:
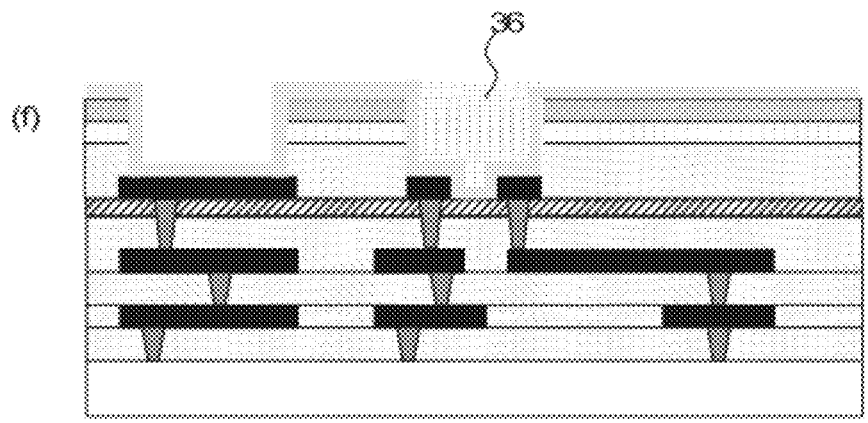
Figure 2:
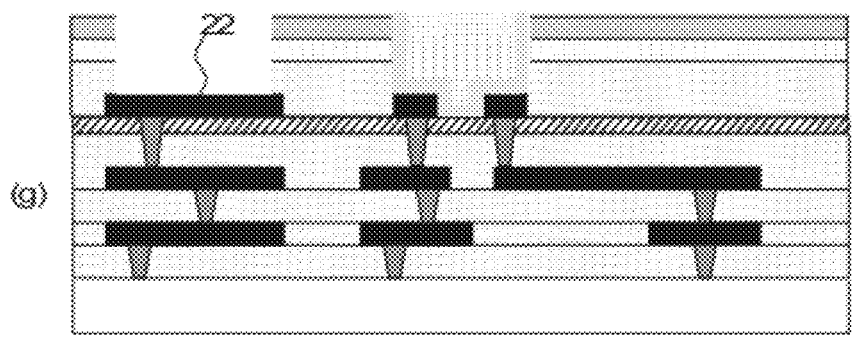
Figure 3:
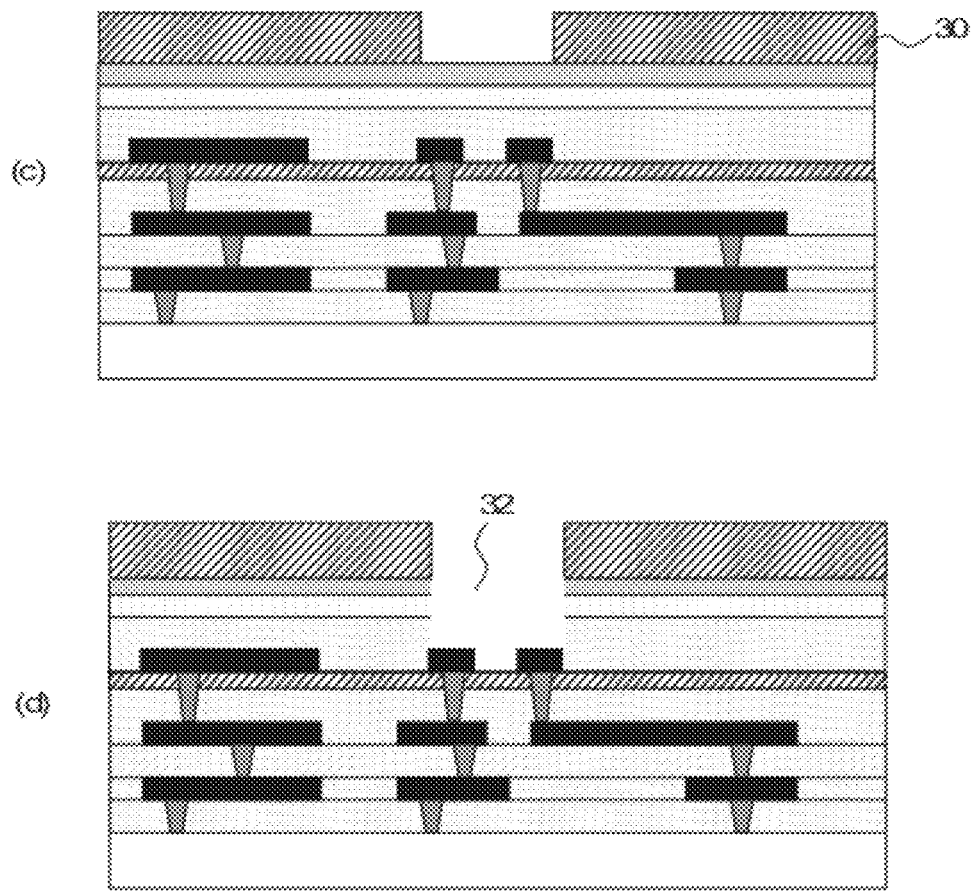
Figure 3:
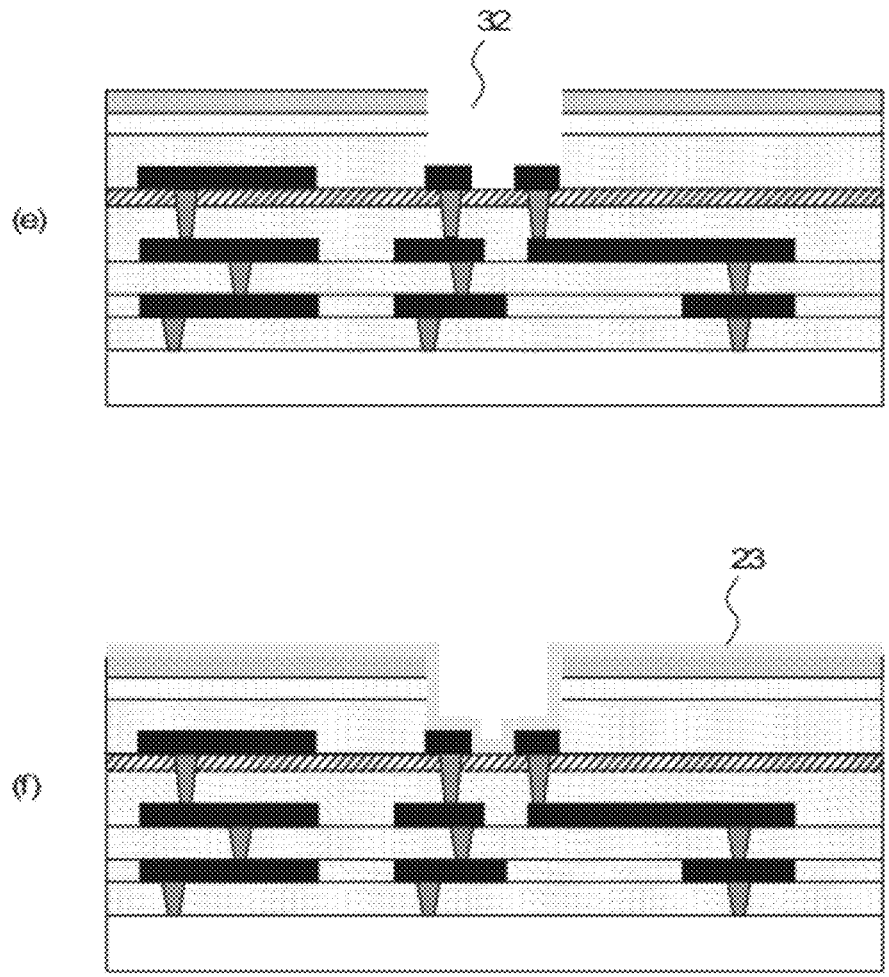
Figure 3:
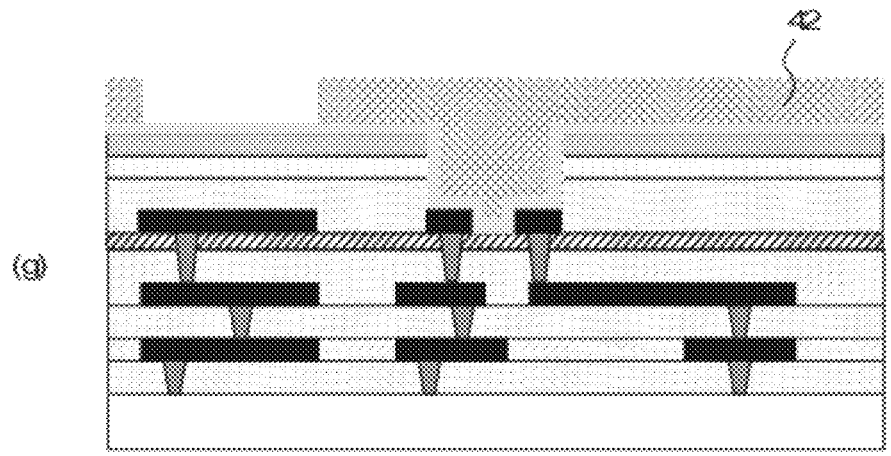
Figure 3:
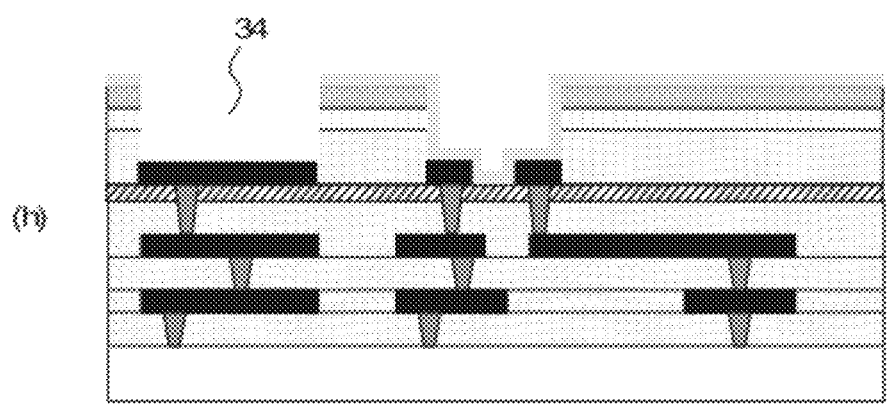
Figure 3:
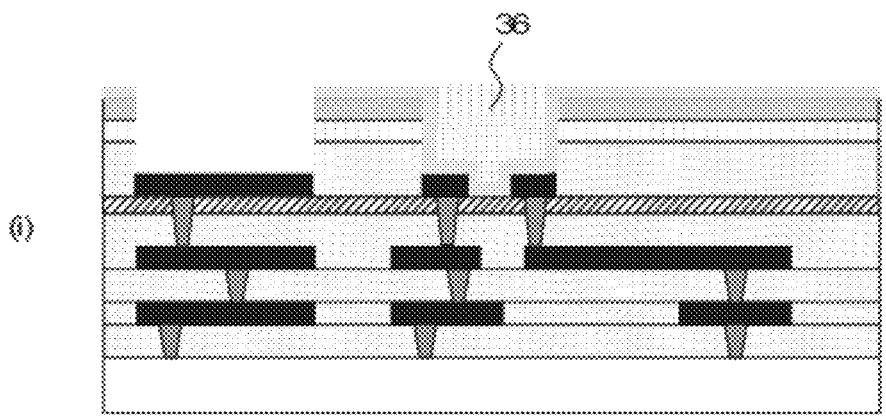
Figure 4:
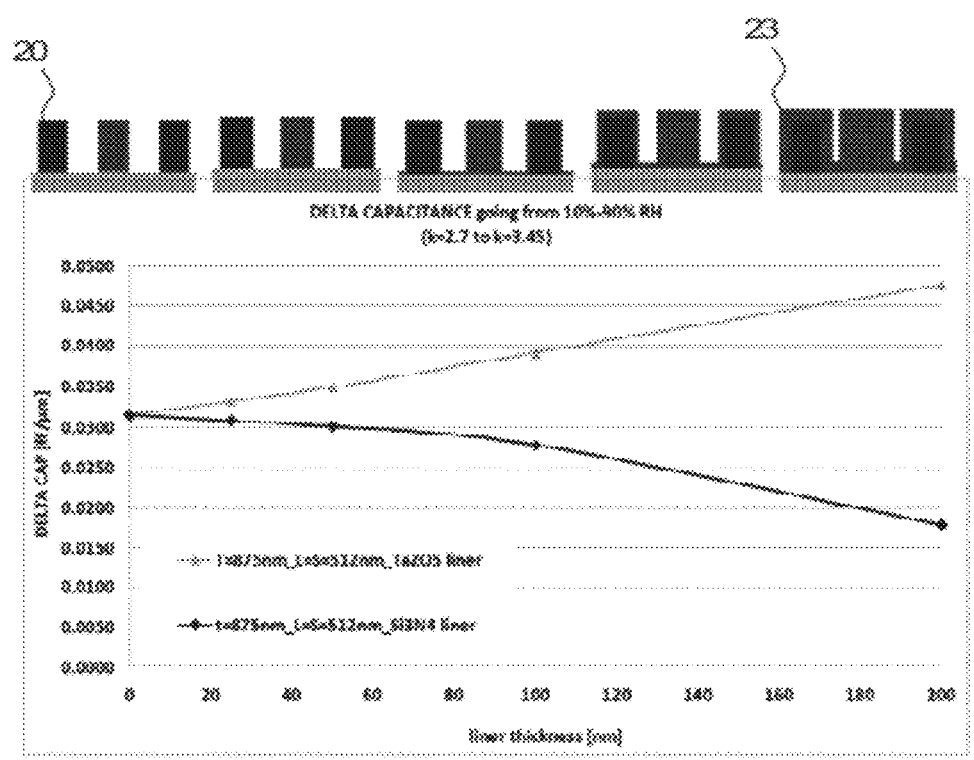

Embodiments of the invention are described in more detail and by way of non-limiting examples with reference to the accompanying drawings, wherein:

FIG. 1 schematically depicts a method of manufacturing an IC according to an embodiment of the present invention;

FIG. 2 schematically depicts a method of manufacturing an IC according to another embodiment of the present invention;

FIG. 3 schematically depicts a method of manufacturing an IC according to yet another embodiment of the present invention; and FIG. 4 depicts a simulation result of the sensitivity of an IC of the present invention having a relative humidity sensor covered by a $Ta_2O_5$ film compared to a relative humidity sensor covered by a $Si_3N_4$ film.

DETAILED DESCRIPTION OF THE DRAWINGS

It should be understood that the Figures are merely schematic and are not drawn to scale. It should also be understood that the same reference numerals are used throughout the Figures to indicate the same or similar parts.

FIG. 1 schematically depicts the various steps of a method of manufacturing an IC with an environmental sensor, i.e. a sensor exposed to the environment of the IC in accordance with an embodiment of the present invention, in which an improved protection against moisture penetrating the internals of the IC is achieved. As shown in step (a), an IC may be provided comprising a substrate 10 onto which a metallization stack is formed. Such a metallization stack typically comprises a stack of patterned metal layers 12 electrically insulated from each other by electrically insulating, i.e. dielectric layers 14. Metal portions in different metallization layers 12 may be conductively coupled to each other by means of vias 16 extending through dielectric layers 14 separating such metal portions from each other. The substrate 10 may be any suitable substrate material, e.g. single crystal Si, SiGe, silicon on insulator and so on, and may carry a plurality of circuit elements such as transistors, diodes and so on.

Equally, the metallization stack may be formed in any suitable manner, and may contain any suitable number of metal layers 12 and dielectric layers 14. It should be understood that three metal layers are shown by way of non-limiting example only.

Each metal layer 12 and each dielectric layer 14 is depicted as a single layer in FIG. 2 for the sake of clarity only. It should be appreciated that such layers may consist of a number of stacked sub-layers, for instance in a submicron CMOS process, stacks of Ti, TiN, AlCu, TiN may be used to define a single metal layer in the metallization stack.

Each of the dielectric layers 14 may also comprise more than a single layer. For instance, such a dielectric layer may be a stack comprising FSG (fluorosilicate glass), $SiO_2$ and HDP oxide (High Density Plasma) any other suitable dielectric material combination. Other suitable materials may also be used.

Similarly, it will be apparent that the vias 16 may be formed from more than a single material. For instance, in the aforementioned CMOS 14 technology, a via 16 may be formed by a Ti/TiN liner and a W plug. Other semiconductor processes may use different materials, e.g. Cu for the metal layers 12 and vias 16.

In FIG. 1, the upper metal layer of the metallization stack comprises a sensor electrode portion 20 and a bond pad portion 22. In a CMOS process, these may be aluminium portions. The sensor electrode portion 20 preferably comprises a pair of laterally separated electrodes, which preferably have a large surface area, e.g. interdigitated (finger) electrodes. An electrically insulating moisture barrier film 23, e.g., a thin dielectric layer, is formed over the patterned upper metallization layer including sensor portion(s) 20 and bond pad portion 22. Such a moisture barrier film 23 may for instance be a $Ta_2O_5$ film, and may be formed using suitable deposition techniques such as plasma vapor deposition or chemical vapor deposition. Chemical vapor deposition is preferred as it yields highly conformal layers that can be formed over stepped surfaces with high resistance to cracking, thereby ensuring a reliable moisture barrier 23.

In step (b), a passivation stack is formed over the metallization stack including the moisture barrier film 23. The formation of the passivation stack may comprise the deposition of a high density plasma oxide 24 followed by an oxide planarization step, e.g. a chemical mechanical polishing (CMP) step, after which a $SiO_2$ layer 26 and a $Si_3N_4$ layer 28 may be deposited to any suitable thickness. In an alternative embodiment, the oxide CMP step is omitted, as it is not essential to the present invention; i.e., an IC having a non-planarized passivation stack may be provided. Other layer materials may also be contemplated for the passivation stack. For instance, a TEOS layer may be added to the stack, e.g. after deposition of the HDP oxide 24, without departing from the teachings of the present invention. It is known per se to the skilled person how to form such a passivation stack such that this will not be elaborated upon for reasons of brevity only.

The method proceeds as shown in step (c), in which a resist 30 is deposited onto the passivation stack and subsequently patterned to leave exposed the parts of the passivation stack over the electrode portion 20. Any suitable resist material may be used for this purpose, e.g. a negative resist or a positive resist material. The resultant structure is subsequently subjected to an etch recipe, e.g. a reactive ion etch (RIE), to selectively remove the respective layers of the passivation stack from over the sensor electrode portion 20 and the bond pad portion 22 such that these portion becomes exposed by trenches 32 and 34 respectively, as shown in step (d). The moisture barrier film 23 may be used as etch stop layer in this process.

Next, as shown in step (e), the patterned resist 30 is stripped from the patterned passivation stack and the trench 32 over the sensor electrode portion(s) 20 is filled with a sensor active material 36, i.e. a material that makes the sensor sensitive to an analyte of interest. In case of a moisture sensor or a liquid immersion sensor, the sensor active material 36 may be a moisture-sensitive material that has a dielectric constant as a function of its moisture content. A non-limiting example of a suitable embodiment of the sensor active material 36 is polyimide.

It is noted that in FIG. 1(*e*) the sensor active material 36 laterally separates the electrode portions 20, i.e. extends beyond the upper surface of these electrode portions. This significantly increases the sensitivity of the sensor. Also, in FIG. 1(*e*), the sensor active material 36 is shown planarized with the planarization stack by way of non-limiting example. It is equally feasible to have the sensor active material 36 extending beyond the planarization stack and laterally over the edges of the trench 32, which can further improve the sensitivity of the sensor comprising the one or more electrode portions 20 and relax the precision requirements of the lithographic step for forming the active sensor material 36 in the trench 32.

Finally, the bond pad portion 22 is exposed by the removal of the electrically insulating moisture barrier film 23 and any other residual layers as is shown in step (f). From hereon, the IC of the present invention may be completed in any suitable manner, e.g. by providing external contacts to the bond pads of the IC that have been symbolized by the single bond pad portion 22. The skilled person will immediately realize that a single bond pad portion 22 has been shown for clarity reasons only and that the IC typically comprises a plurality of bond pad portions 22.

An alternative embodiment of a manufacturing method of the present invention is shown in FIG. 2. In step (a), an IC may be provided comprising a substrate 10 onto which a metallization stack is formed in the same manner as described in the detailed description of step (a) of FIG. 1. However, an etch stop layer 40 is added to the metallization stack directly underneath the patterned upper metallization layer, i.e. directly underneath the one or more sensor electrode portions 20 and the bond pad portion 22. Such an etch stop layer 40 may for instance be formed by altering the process step for the formation of the vias 16. Non-limiting examples of suitable materials for the etch stop layer include silicon nitride ($Si_3N_4$) and silicon-rich oxide ($SiO_x$, $x<2$). Another difference is that the moisture barrier film 23 is not formed at this stage.

In step (b), the passivation stack is formed as previously explained and in step (c) the trenches 32 and 34 are formed over the one or more sensor electrode portions 20 and the bond pad portion 22 as previously explained.

In step (d), the patterned resist 30 is stripped from the passivation stack, after which the moisture barrier film 23 is deposited over the resulting structure as shown in step (e). It is preferred that this film 23 is a $Ta_2O_5$ film formed by chemical vapor deposition (CVD) to prevent cracking in this film, which is known to be a problem in moisture barrier films such as $Ta_2O_5$ films deposited using alternative techniques. Also, CVD films are highly conformal, thus improving the planarity of the deposited moisture barrier film 23.

Next, as shown in step (f), the sensor active material 36 is formed in the trench 32 over the one or more sensor electrode portions 20. The sensor active material 36 also acts as a protective mask for the moisture barrier film 23 formed inside the trench 32. This is relevant for the final step (g), in which the moisture barrier film 23 is removed from the remainder of the passivation layer and the bond pad portion 22 to expose the bond pad portion 22 as previously explained. From hereon, the IC may be completed using standard manufacturing techniques as previously explained. In an alternative to the step shown in FIG. 2(*g*), the moisture barrier film 23 may be retained on the upper surface of the passivation stack, i.e. may be selectively removed from the trench 34 only. In yet an alternative embodiment, the moisture barrier film 23 may be selectively removed from the bond pad only, thus keeping the upright walls of the trench 34 lined with the moisture barrier film 23. It will be apparent to the skilled person that the more area of the contact surface of the IC of the present invention with the environment is protected by the moisture barrier film 23, the more robust the IC becomes against moisture exposure.

Yet another embodiment of the method of the present invention is shown in FIG. 3. The first steps of the method are identical to the steps (a) and (b) as shown in FIG. 2 and are therefore not shown again for the sake of brevity. The method proceeds to step (c) in which a patterned resist 30 is formed over the passivation stack. The patterned resist 30 comprises an opening 32 over the area of the passivation stack above the one or more sensor electrode portions 20 but covers the area of the passivation stack over the bond pad portion 22.

Next, the trench 32 is formed in the passivation stack to expose the one or more electrode portions 20. The resultant structure is shown in step (d). The advantage of forming the trench 32 in a separate step is that because the aspect ratios of the trenches 32 and 34 may be different, it is difficult to provide an etch recipe that does not laterally overetch the narrower of the two trenches, typically the first trench 32 over the one or more electrode portions 20. By forming the trenches 32 and 34 in separate steps, the etch recipes may be optimized for each trench, thus providing improved control over the trench forming process. Etch recipe optimization is a routine task for the skilled person and will therefore not explained in further detail for the sake of brevity only.

After the patterned resist 30 is stripped from the passivation stack as shown in step (a), the method proceeds to step (f) in which the moisture barrier film 23 is formed over the resultant structure. Again, a CVD $Ta_2O_5$ film is preferred because of its high conformality and its resistance to cracking on stepped surfaces.

Next, a further patterned resist 42 is deposited over the moisture barrier film 23, leaving exposed the region above the bond pad portion 22. This is shown in step (g). Any suitable resist material may be used for the further patterned resist 42, e.g. the same material as used for the patterned resist 30. The trench 34 exposing the bond pad portion 22 is subsequently formed using a suitable etching step, preferably optimized with respect to the aspect ratio of the trench 34. A non-limiting example of such an etch step is a reactive ion etch stopping on the bond pad metal, e.g. Al, to remove the passivation stack in the areas exposed by the further patterned resist 42, after which the further patterned resist 42 is stripped off the moisture barrier film 23 in any suitable manner, thus resulting in the structure shown in step (h) of FIG. 3.

Finally, the sensor active material 36 is formed in the trench 32 to complete the sensor of the IC of the present invention, as shown in step (i). The IC may again be completed in any suitable manner as previously explained.

In an embodiment of the present invention, the sensor comprises a pair of interdigitated electrodes 20, e.g. meandering or finger electrodes in which the electrodes are electrically insulated from each other by the moisture-adsorbent sensor active material 36, such as polyimide or another suitable electrically insulating material. This effectively provides a capacitor having large surface area capacitor plates in the form of interdigitated electrodes 20, with the sensing material 36 acting as the dielectric of the capacitor. Alternatively, the sensor electrode portion 20 may be an extended gate of a transistor on the substrate 10, in which case changes in the content of the analyte of interest in the sensor active material 36, e.g. moisture content, will affect the gate potential sensed by the transistor. Other arrangements will be apparent to the skilled person.

EXAMPLE

A simulation of a number of ICs having a relative humidity sensor with interdigitated electrodes 20 covered by a $Ta_2O_5$ film 23 of varying thicknesses (triangles) and a number of ICs having a relative humidity sensor with interdigitated electrodes 20 covered by a $Si_3N_4$ film with varying thicknesses is provided using the Rafael™ simulation software. The software was calibrated using actual IC measurement results at selected dielectric layer thicknesses at 30% and 70% relative humidity.

In the simulation, for each thickness, the corresponding IC was subjected to an atmosphere having a relative humidity that was gradually increased from 10-90% and the difference in capacitance between the extreme values of this range was measured. The simulation results are shown in FIG. 4. The results for the $Ta_2O_5$-covered sensor are shown by the triangles and the results for the $Si_3N_4$-covered sensor are shown by the squares. It will be immediately apparent that for the $Ta_2O_5$ layer 23 the sensor sensitivity increases with the thickness of this layer, whereas the opposite effect is demonstrated for a sensor covered by a $Si_3N_4$ layer of the same thickness. Hence, in addition to providing improved moisture barrier properties, the $Ta_2O_5$ layer 23 also improves the sensitivity of the relative humidity or moisture sensor of the IC of the present invention.

Although the described embodiments have been limited to providing the IC of the present invention with a single environmental sensor, it will be appreciated that other sensors may be included in the IC design without departing from the scope of the present invention.

The IC of the present invention may be integrated in any suitable electronic device, e.g. a mobile communication device such as a mobile phone, personal digital assistant and so on, or may be used as a tag for an article for monitoring purposes, in which case the IC may be extended with RF functionality, e.g. an RF transceiver communicatively coupled to the sensor(s) of the IC.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or an preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An integrated circuit comprising:
   a substrate carrying a plurality of circuit elements;
   a metallization stack interconnecting the circuit elements, the metallization stack comprising a patterned upper metallization layer comprising at least one sensor electrode portion and a bond pad portion, at least the at least one sensor electrode portion of the patterned upper metallization layer being covered by a moisture barrier film; and
   a passivation stack covering the metallization stack including the moisture barrier film, the passivation stack comprising a first trench exposing the at least one sensor electrode portion and a second trench exposing the bond pad portion, the first trench being filled with a sensor active material,
   wherein the integrated circuit is configured as a moisture sensor and the sensor active material is a moisture-sensitive material that has a dielectric constant as a function of its moisture content, and
   wherein the sensor electrode portion comprises a pair of laterally separated electrodes which form interdigitated finger electrodes.

2. The integrated circuit of claim 1, wherein the moisture barrier film comprises a $Ta_2O_5$ film.

3. The integrated circuit of claim 2, wherein the $Ta_2O_5$ film is a chemical vapor deposited film.

4. The integrated circuit of claim 1, wherein the patterned upper metallization layer comprises aluminum.

5. The integrated circuit of claim 1, wherein the patterned upper metallization layer is covered by the moisture barrier film apart from the bond pad portion exposed by the second trench.

6. The integrated circuit of claim 1, wherein the pair of electrodes of the at least one sensor electrode portion is laterally separated by the sensor active material.

7. A method of manufacturing an integrated circuit having a sensor, comprising:
   providing a substrate carrying a plurality of circuit elements;
   forming a metallization stack over the substrate interconnecting the circuit elements, the metallization stack comprising a patterned upper metallization layer comprising at least one sensor electrode portion and a bond pad portion;
   forming a moisture barrier layer covering at least the at least one sensor electrode portion of the patterned upper metallization layer;
   forming a passivation stack over the metallization stack including the moisture barrier film;
   patterning the passivation stack to form a first trench exposing the at least one sensor electrode portion and a second trench exposing the bond pad portion; and
   filling the first trench with a sensor active material,
   wherein the integrated circuit is configured as a moisture sensor and the sensor active material is a moisture-sensitive material that has a dielectric constant as a function of its moisture content, and
   wherein the sensor electrode portion comprises a pair of laterally separated electrodes which form interdigitated finger electrodes.

8. The method of claim 7, wherein the step of patterning the passivation stack to form a first trench exposing the at least one sensor electrode portion and a second trench exposing the bond pad portion comprises simultaneously forming the first trench and the second trench.

9. The method of claim 7, wherein the step of forming the moisture barrier layer comprises depositing a $Ta_2O_5$ film.

10. The method of claim 9, wherein the step of depositing the $Ta_2O_5$ film comprises depositing the film by chemical vapor deposition.

* * * * *